United States Patent [19]

Tanaka et al.

[11] Patent Number: 5,290,514

[45] Date of Patent: Mar. 1, 1994

[54] DRY ANALYSIS ELEMENT HAVING A CONSTANT BLANK VALUE AND PROCESS FOR PREPARING THE SAME

[75] Inventors: Mitsutoshi Tanaka; Takaki Arai; Takeshi Igarashi; Kenichi Sawada, all of Saitama, Japan

[73] Assignee: Fuji Photo Film Co., Ltd., Kanagawa, Japan

[21] Appl. No.: 959,169

[22] Filed: Oct. 9, 1992

Related U.S. Application Data

[63] Continuation of Ser. No. 486,057, Feb. 27, 1990, abandoned.

[30] Foreign Application Priority Data

Feb. 27, 1989 [JP] Japan .................. 1-45730

[51] Int. Cl.⁵ ............... G01N 21/01; G01N 31/22
[52] U.S. Cl. ........................... 422/56; 422/57; 422/58; 422/61; 435/805; 436/166; 436/169; 436/170
[58] Field of Search ............. 422/56–58, 422/61; 435/805; 436/166, 169, 170

[56] References Cited

U.S. PATENT DOCUMENTS

| | | | |
|---|---|---|---|
| Re. 30,267 | 5/1980 | Bruschi | 422/56 X |
| 2,823,984 | 2/1958 | Maurodneanu | 436/169 X |
| 3,992,158 | 11/1976 | Przybylovicz et al. | 422/58 X |
| 4,042,335 | 7/1977 | Clément | 422/56 |
| 4,144,306 | 3/1979 | Figueras | 422/56 |
| 4,292,272 | 9/1981 | Kitajima et al. | 422/56 X |
| 4,548,905 | 10/1985 | Wu | 422/56 X |
| 4,567,024 | 1/1986 | Koyama et al. | 422/56 |
| 4,568,647 | 2/1986 | Sanford | 422/56 X |
| 4,689,309 | 8/1987 | Jones | 422/56 |
| 4,772,561 | 9/1988 | Genshaw | 422/56 X |
| 4,783,315 | 11/1988 | Arai et al. | 422/56 |
| 4,786,605 | 11/1988 | Mauck et al. | 422/56 X |
| 4,868,131 | 9/1989 | Hiratsuka | 422/57 X |
| 5,006,458 | 4/1991 | Kato et al. | 422/56 X |

*Primary Examiner*—James C. Housel
*Assistant Examiner*—Arlen Soderquist
*Attorney, Agent, or Firm*—McAulay Fisher Nissen Goldberg & Kiel

[57] ABSTRACT

A dry analysis element which gives a calibration curve having a constant blank value for every lot and can be used without the need of correction of the internal calibration curve memorized in an analyzer. The dry analysis element including a water-permeable layer which contains: a reagent composition capable of producing an optically detectable substance in the presence of a predetermined analyte in an aqueous sample; and a fogging agent selected from the group consisting of the optically detectable substance and a material which is detectable by the same method for detecting the optically detectable substance. Also provided is a process for preparing the analysis element.

22 Claims, 1 Drawing Sheet

DRY ANALYSIS ELEMENT HAVING A CONSTANT BLANK VALUE AND PROCESS FOR PREPARING THE SAME

This is a continuation of application Ser. No. 07/486,057, filed Feb. 27, 1990, now abandoned.

BACKGROUND OF THE INVENTION

1. Field of the Invention

The present invention relates to a dry analysis element having a constant blank value on a calibration curve, and process for making the dry analysis element. More particularly, the invention provides a dry analysis element which is conveniently used in an automated analyzer system having a fixed calibration curve, and also provides a process for preparing such a dry analysis element.

2. Prior Art Statement

Dry chemistry has been increasingly used in various clinical tests in recent years since they are easily handled and give results instantaneously. In order that the dry chemistries are handled more easily in a small-scale hospital by medical personnel, it is desirous that they can be used without the need of correction operation. This means that the test system need not be adjusted by using a standard solution or like control before it is used for practical test. An important merit of the systems in which dry chemistries are used is that a sample can be tested immediately at any desired time. In other words, a dry chemistry is used particularly conveniently when a small number of samples, sometimes a single sample, is subjected to test. By such a procedure, a real-time test result can be obtained to realize more effective medical treatment. However, need of correction operation obstructs a prompt test. If it is required to test individual samples promptly at any desired time, it becomes a problem when the correction operation of the system should be conducted or at what time intervals correction operations should be conducted. Since such a correction operation requires time and cost, need of correction operation poses a serious problem in case where the number of samples to be tested is so small as only one or two a day as is often a case in an individual doctor's office. Accordingly, if the correction operation becomes unnecessary, it contributes realization of effectual medical treatment at an extent more than that attainable by an improvement in prompt operation of the system. Although it is particularly preferable for the user if the correction operation of the system becomes not requisite, provision of such an analysis element imposes an extreme burden on the maker. This is because the analysis elements are usually produced by lots which are differentiated with each other due to the differences in used materials and variations of factors in the producing steps.

In automated analysis systems using dry chemistries which do not require daily correction operations, calibration curves are usually memorized in the analyzers per se. The calibration curves mean the graphs, numerical tables or equations indicating the interrelations between the quantities of individual analytes and the optical densities (hereinafter referred briefly to as "O.D.") of the coloring (including color changes and generation of fluorescent lights), and are usually obtained by the correction operations. In order to exempt the correction operation in a system in which a dry chemistry is used, the calibration curve must be obtained by the maker which is memorized in the analyzer. The thus memorized calibration curve will be referred to as internal calibration curve.

In order to guarantee the performance characteristics of a system in which an internal calibration curve is memorized, the characteristics of the available analysis elements shall not be shifted from the memorized internal calibration curve and the characteristics of the available analysis elements shall not be changed with the lapse of time. Non-shifting from the internal calibration curve means that the practical calibration curves of commercially available analysis elements are coincident with the memorized internal calibration curve. In general, properties of industrial products are dispersed and industrial standards are stipulated for individual products for standardization of industrial products. Likewise, coincidence of calibration curve means that the difference between the practical calibration curve and the memorized internal standard curve is within the standard allowable error range. Of course, the standard allowable error range must be narrow enough not to cause any problem in practice even if the properties of the products are changed within this range.

The calibration curves are linear in many cases, and can be represented by a linear equation of $y = ax + b$ when the amounts (density, active value, activity, etc.) of analytes are plotted along the x-axis (abscissa) and the O.D. of coloring or like are plotted along the y-axis (ordinate). In the equation set forth above, slope a indicates the extent of changeability of O.D. in terms of the quantitity of the analyte to be analyzed, and thus a will be referred to as sensitivity constant. In the same equation, b indicates the blank value when the quantity of the analyte is zero, and thus b will be referred to as blank constant.

In the systems wherein dry chemistries are used, since the optical densities of reflected lights are usually measured, there are often cases where the obtained calibration curves are not linear. In such a case, the calibration curves may be transfigured into linear by transforming the same while making use of an interrelation between the reflected light and the transmitted light. However, rarely is a linear calibration curve obtained. It is considered that such a result is due to the fact that the total yield of the complicated reactions in the plural layer is not 100 percent. Even when the obtained calibration curve is a slightly arcuated curve, it may be deemed expediently as approximate to linear and expressed by the two parameters, i.e. the sensitivity constant a and the blank constant b. Particularly when the products are the same kinds, such an approximation is acceptable, since the curvature of the arcuated curve are identical if the structure of layers and the reaction mechanisms are identical.

The sensitivity constant a and the blank constant b are varied depending on the variations in processing steps and properties of the used raw materials. Particularly, the blank constant b is affected by the variation in properties of the used raw materials. If the blank constant is varied for every lot, the internal calibration curve must be altered for every lots or the internal calibration curve must be corrected using a standard solution, leading to the result that the merit of the dry chemistry is injured seriously.

In view of the above, it is desirous that the raw materials used for the preparation of analysis element should have constant purities, and preferably be as pure as possible. However, raw materials usually contain various impurities. Particularly, raw materials of natural origin or materials which tend to decompose to produce decomposition products during the preparation steps or storage time contain different quantities of impurities. Some examples of unstable raw materials will be set forth below.

(1) Since the bond gelatine forms a bone together with calcium (Ca), it contains Ca. When the bone gelatine is used as a raw material for the preparation of an analysis element for analyzing Ca, the blank constant b is affected significantly by the Ca contained as an impurity in the raw bone gelatine.

(2) Since diazonium salts used as the color formers are unstable, portions thereof are decomposed during the refining step to form dyes having absorption peaks within the visible range. Accordingly, when a diazonium salt is used for the preparation of an analysis element for analyzing bilirubin, the blank constant b is affected by the dye formed by decomposition of the diazonium salt.

(3) When a color former of redox system wherein hydrogen peroxide is used as an intermediate product is used, the blank constant b is sometimes affected by oxides contained in raw materials.

Since the blank constant b is varied by the above and other factors, it is desirous that the used raw materials are sufficiently refined to use at high purities in order to remain the blank constant at a constant value. However, purification of raw materials causes increase in cost, and when the raw materials are used without purifying them, the produced analysis element does not pass the quality control inspection so frequently as to lead an increase in cost of the acceptable product. There is, therefore, a demand for maintaining the blank constant b at a constant value without increasing the cost for preparing the raw materials.

OBJECTS AND SUMMARY OF THE INVENTION

An object of this invention is to provide a dry analysis element which gives a calibration curve having a constant blank value for every lot.

A more specific object of this invention is to provide a dry analysis element which can be used in an analyzer wherein a fixed internal calibration curve is used without the need of correcting the internal calibration curve.

A further object of this invention is to provide an analysis element which gives a calibration curve having a constant blank value without causing increase in production cost due to need of purification of raw materials.

A still further object of this invention is to provide an analysis element which gives a calibration curve having a constant blank value for every lot without the need of strict purification or selection of raw materials.

An additional object of this invention is to provide a process for preparing such a dry analysis element.

The aforementioned objects of this invention are achieved by the provision of a dry analysis element comprising at least one water-permeable layer containing a fogging agent.

The fogging agent used in this invention is a component added to raise the blank constant or blank value of the calibration curve of the analysis element, and selected from the following two materials.

(1) A material, such as a dye (hereinafter referred to as "formed dye"), which is the same as that formed by the coloring reaction in the particular analysis element, the formed dye being optically detectable.

(2) An optically detectable material, such as a dye (hereinafter referred to as "different dye"), which is different from the formed dye.

DETAILED DESCRIPTION OF THE INVENTION

Figure 1:
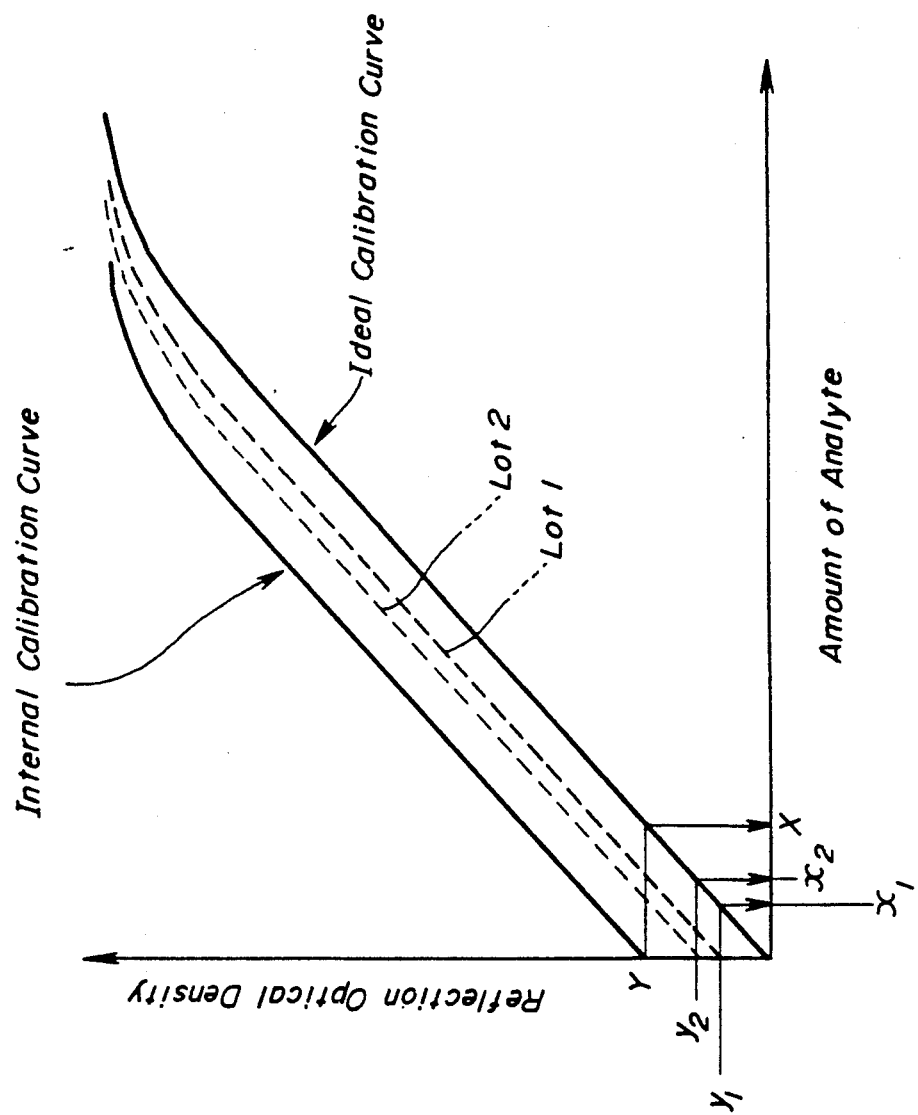
FIG. 1 is a graphical representation given for understanding the principle of the invention.

Initially, the principle of this invention will be described with reference to FIG. 1.

The quantities of analytes in samples are plotted along the abscissa of FIG. 1, and the optical densities of the reflected lights are plotted along the ordinate. The ideal calibration curve having a blank value of zero passes the origin, but practical calibration curves have individual blank values. If the blank values are not differentiated for every lot, single calibration curve is properly memorized in the analyser as the internal calibration curve. However, due to variations in impurities in the used raw materials, Lot 1 has a blank value of $y_1$ and Lot 2 has a different blank value of $y_2$. When the structure of the layers in the analysis elements is identical and the conditions for measurement are not changed, the difference between these blank values substantially correspond to the quantities of the impurities contained in raw materials in respective analysis elements. Specifically, the blank value $y_1$ of Lot 1 substantially corresponds to the quantity $x_1$ of the impurity in Lot 1, and the blank value $y_2$ of Lot 2 substantially corresponds to the quantity $x_2$ of the impurity in Lot 2. According to an important aspect of this invention, the blank value of the internal calibration curve is set to a sufficiently high value (Y), and a standard quantity, X corresponding to the blank value Y is calculated. The Lot 1 is added with an fogging agent in an amount of $X - x_1$, and the lot 2 is added with the fogging agent in an amount of $X - x_2$. Each lot is added with the fogging agent in an amount corresponding to the difference between the standard quantity X and the quantity of existing impurity. As the result of the addition of the impurity, each lot gives a calibration curve having a blank value which is coincident with that of the internal calibration curve to make it possible to exempt the correction operation for each lot.

A preferred embodiment of this invention will now be described. A lot of an analysis element is prepared by using raw materials purified or selected to have purities which do not cause increase in production cost, and the blank value of the calibration curve of the lot is obtained by a preliminary test. The preliminary test may be conducted by a wet process using a solution or by a dry process using a multi-layered analysis element which is prepared for the calibration purpose. The difference between the blank value obtained by the preliminary test and the blank value of the internal calibration curve is calculated, and a multi-layered analysis element is prepared by adding the fogging agent as defined above, in an amount for compensating the difference, to a water-permeable layer containing a reagent composition or an additional water-permeable layer.

As will be understood from the foregoing, in practice of this invention, it is essential that the blank value of the internal calibration curve is sufficiently higher than the variation range of the blank value of most of the multi-layered analysis element prepared by using the raw materials purified or selected to have purities which do not cause increase in production cost. In other words, the blank value of the internal calibration curve is set to a value approximate to the highest blank value occasionally found in some lots of analysis element. For example, the blank value of the internal calibration curve is as high as about 1.5 to 3 times of the ordinary variation range found in most lots of analysis element. If the blank value of the internal calibration curve is not higher than the expected variation range of most of the multi-layered analysis element, it becomes meaningless to apply the principle of this invention. In other words, a fogging agent is added in an amount for raising the blank value of the calibration curve in each lot sufficiently higher than the initial blank value measured by the preliminary test, and the internal calibration curve of the system, in which the analysis element of the invention is used, is set to the thus raised blank value. Of course, such a lot of multi-layered analysis element that has a blank value higher than the thus set blank value of the internal calibration curve is rejected as an off-grade lot, since the present invention cannot be applied to the analysis elements of such lot.

A formed dye or a different dye may be used as the fogging agent.

Specific examples of the formed dye which may be used as the fogging agent in the present invention include:

(1) Dyes formed as oxides of leuco dyes (arylimidazole leuco dyes disclosed, for example, in U.S. Pat. No. 4,089,747 and Unexamined Japanese Patent Publication No. 193352/1984 (corresponding to European Patent Publication 0122641A));

(2) Diazo dyes produced by coupling of diazonium salts, such as coupling reaction products of bilirubin and diazonium salts;

(3) Azomethine dyes produced by coupling between oxidized hydrogen donors and couplers, such as those produced from 4-aminoantipyrine and phenols or naphtols, and ketomethylene dyes;

(4) Formazan dyes produced in the presence of reducing co-enzymes (such as NADH or NADPH) and electron carriers (such as diaphorase);

(5) Materials which emit dissociated anions absorbing visible lights, such as p-nitrophenol, o-chloro-p-nitrophenol and p-nitroaniline; and (6) Colored metal complexes, such as calcium complex of o-cresolphthalein Complexon (3,3'-bis[N,N-di(-carboxymethyl)aminoethyl]-o-cresolphthalein).

Other than dyes, optically detectable materials may be used as the fogging agent, the examples being those which absorb ultraviolet rays, such as NADH.

Specific example of different dye which may be used as the fogging agent in the present invention include Ponseau 3R, 2,2'-bis[3-carboxy-1-(4-sulfophenyl)-pyrazolin-5-on]trimethineoxonol, N-[4-(4',4"-dianilinodiphenylmethylene)benzo] anilinium chloride, 2-p-dimethylaminophenylazo-3-methylbenzothiazolium methylsulfate, 1-methyl-2-(2'-methyl-4'-(N-(2"-chloroethyl)-N-ethylamino)styryl)-3,3-dimethylindolenium chloride, N-(1-ethoxy-6-diethylamino-3-oxazinilidene)-diethylammonium chloride, [2-[4'-(2",4"'-dicyanophenylazo)-N-ethylanilino]ethyl]trimethylammonium methylsulfate, 1-[3'-(dimethylammonio)propyl-]aminoanthraquinone dimethylsulfate. It is preferred to use a material which does not hinder the reaction in the analysis element and is stable during the storage time. A light absorbing pigment, such as carbon black, may also be used. Another suitable dye may be selected from known dyes described, for example, in Dye Handbook (edited by Ohkawara et al., and published by KODANSHA in 1988).

The present invention may be applied to various dry analysis elements disclosed, for example, Japanese Patent Publication No. 21677/1978 (corresponding to U.S. Pat. No. 3,992,158) and Unexamined Japanese Patent Publication Nos. 164356/1980 (corresponding to U.S. Pat. Nos. 4,292,272) and 222769/1985 (corresponding to European Patent publication No. 0162302A). For example, the present invention may be applied to the preparation of analysis elements having the following laminated structures.

(1) An analysis element comprising a liquid spreading layer (hereinafter referred to as "spreading layer") containing the aforementioned reagent composition and laminated on a water-impermeable and light-transmitting support;

(2) An analysis element comprising a water-impermeable and light-transmitting support, a reagent layer laminated on the support, and a liquid spreading layer laminated on the reagent layer;

(3) An analysis element comprising a water-impermeable and light-transmitting support, a detection layer laminated on the support, a reagent layer laminated on the detection layer and a liquid spreading layer laminated on the reagent layer;

(4) An analysis element comprising a water-impermeable and light-transmitting support, a reagent layer laminated on the support, a light-reflecting layer laminated on the reagent layer and a liquid spreading layer laminated on the light-reflecting layer;

(5) An analysis element comprising a water-impermeable and light-transmitting support, a detection layer laminated on the support, a reagent layer laminated on the detection layer, a light-reflecting layer laminated on the reagent layer and a liquid spreading layer laminated on the light-reflecting layer;

(6) An analysis element comprising a water-impermeable and light-transmitting support, a detection layer laminated on the support, a light-reflecting layer laminated on the detection layer, a reagent layer laminated on the light-reflecting layer and a spreading layer laminated on the reagent layer.

The present invention may also be applied to multi-layered analysis elements having the structures similar to those as set forth in (1), (2) and (4) and further including a water-absorbing layer interposed between the support and the liquid spreading layer or the reagent layer. A blood corpuscle filtering layer may be provided between the reagent layer and the detection or spreading layer in either one of the analysis elements as set forth in (2) to (4). A blood cell filtering layer or an interferant material removing layer may be provided between the light reflecting layer and the detection, reagent or spreading layer or between the reagent layer and the detection layer or between the reagent layer and the spreading layer in either one of the analysis elements as set forth in (4) to (6).

In the structures set forth above, layers other than the support are water-permeable layers, and may be a porous layer comprised of a porous medium or a non-porous layer comprised of a hydrophilic polymer binder. A porous layer or a non-porous layer may be selectively used depending on the function required for each layer. The present invention may also be applied to analysis elements having structures similar to those as set forth in (1) to (6) except that the support is water-permeable or no support is used.

The fogging agent may be added to any water-permeable layer, other than the support, provided that the aimed object can be achieved. However, it is generally preferred that the fogging agent is added to the reagent layer containing the detection reagent composition, or to the detection layer, or to the water-absorbing layer.

In general, the detection layer contains substantially no detection reagent, and is a layer into which the dye formed in the presence of the analyte permeates and then detected O.D. through the light-transmitting support, and usually composed of a hydrophilic polymer binder. The water-absorbing layer generally contains substantially no detection reagent and is a layer into which diffusion of the dye formed in the presence of the analyte does not occur substantially, and usually composed of a swellable hydrophilic polymer binder.

The analysis element need not have the support when at least one of the water-permeable layers is self-supporting.

It is preferred that a substantially constant amount per unit area of the spotted sample liquid is provided through the spreading layer to the adjacent water-permeable layer. Preferable speading layers are porous layers made of fibrous materials, such as woven fabrics disclosed in Unexamined Japanese Patent Publication No. 164356/1980 (corresponding to U.S. Pat. No. 4,292,272) and knitted fabrics disclosed in Unexamined Japanese Patent Publication No. 222769/1985 (corresponding to European Patent Publication No. 0162302A). The woven or knitted fabrics may be subjected to glow discharge treatment as disclosed in Unexamined Japanese Patent Publication No. 66359/1982 (corresponding to U.S. Pat. No. 4,783,315). The spreading layer may contain a hydrophilic polymer or a surfactant to control the spreading area or spreading rate.

An adhesive layer for adhering and laminating the spreading layer may be applied on the reagent, light-reflecting, filtering, water-absorbing or detection layer. The adhesive layer may be composed of a hydrophilic polymer binder, such as gelatine or derivatives of gelatine, which can adhere to the porous layer when wetted with water. The fogging agent may be added to the adhesive composition used as the adhesive layer.

The analysis element prepared in accordance with the principle of this invention may have a light-reflecting layer. The light-reflecting layer may be interposed between the reagent layer and the detection layer, or may be interposed between the reagent layer and the spreading layer. The light-reflecting layer serves as a layer for reflecting light or for providing a background while shielding the color of the sample solution supplied on the spreading layer by spotting, for example, red color of hemoglobin and yellow color of bilirubin when the sample is the whole blood, whereby a detectable change, i.e. color change or color generation, occurred in the detection layer or the reagent layer is reflected and measured from the support side. It is preferred that the light-reflecting layer is a water-permeable layer in which light reflectable fine particles, such as titanium dioxide or barium sulfate, are dispersed in a hydrophilic polymer which serves as a binder.

The water-permeable layer including the reagent layer in the analysis element prepared by this invention contain a reagent composition which forms an optically detectable substance, such as a dye, in the presence of the predetermined analyte contained in an aqueous sample. Examples of the reagent composition include reagent compositions which produce dyes by oxidation of leuco dyes (for example, triarylimidazole leuco dyes disclosed in U.S. Pat. No. 4,089,747 and diarylimidazole leuco dyes disclosed in Unexamined Japanese Patent Publication No. 193352/1984 (corresponding to European Patent Publication No. 0122641A)); reagent composition containing a diazonium salt which produces a diazo dye by coupling with a coupler; reagent composition containing a chromogen compound and a coupler compound which produces a dye by coupling an oxidized chromogen compound with the coupler compound (for example, 4-aminoantipyrines and phenols or naphtols); reagent composition each composed of a compound which can produce a dye in the presence of a reducing co-enzyme and an electron carrier; and a compound which can form a colored complex with a metal. When the analysis element is an element for analyzing the enzyme activity, a self-coloring substrate for releasing a colored material, such as p-nitrophenol, may be contained in the reagent or spreading layer.

The reagent composition may contain an enzyme which may be selected from the group as disclosed on pages 5 to 7 of the specification of the European Patent Publication No. 0226465A which will be incorporated herein as a reference.

The reagent composition may be totally contained in a non-porous layer composed of a hydrophilic polymer binder. Examples of the hydrophilic polymer binder which may be used for this purpose include gelatine, derivatives of gelatine such as phthalated gelatine, derivatives of cellulose such as hydroxyethyl cellulose, agarose and acrylamide or methacrylamide polymers including co-polymers with various vinyl monomers. The fogging agent may be added to the coating solution for forming the non-porous layer containing the reagent composition.

All or a portion of the reagent composition may be contained in a porous layer. All or a portion of the reagent composition, which is colored in the presence of a specific analyte in the sample liquid, may be contained in the porous layer by applying a porous spreading layer which is preliminarily impregnated with a solution or suspension of the reagent composition on another water-permeable layer, for example on the reagent layer, by the method as disclosed in Unexamined Japanese Patent Publication No. 164356/1980 (corresponding to U.S. Pat. No. 4,292,272).

All or a portion of the fogging agent may be contained in a porous layer. The fogging agent may be added to a solution or suspension of the reagent composition which is preliminarily impregnated into the porous layer, or may be added to a separate composition, other than the reagent composition, which is impregnated into the porous layer.

A porous layer which does not contain the reagent composition may be applied on another water-permeable layer (for example, an adhesive or water-absorbing layer) by the step as disclosed in Unexamined Japanese Patent Publication No. 164356/1980 (corresponding to U.S. Pat. No. 4,292,272), and then a solution or suspension of the reagent composition may be impregnated into the porous layer. The fogging agent may be added to a solution or suspension of the reagent composition which is preliminarily impregnated into the porous layer, or may be added to a separate composition, other than the reagent composition, which is impregnated into the porous layer.

Otherwise, the reagent composition may be contained substantially in the porous layer by coating a uniform layer composed of a hydrophilic polymer binder and containing the reagent composition, and then applying a porous layer which does not contain the reagent composition on the uniform layer of hydrophilic polymer binder by the step as disclosed in Unexamined Japanese Patent Publication No. 164356/1980 (corresponding to U.S. Pat. No. 4,292,272). The fogging agent may be added to the coating composition containing the reagent composition.

Coating of the reagent layer, coating of other compositions for forming other non-porous and water-permeable layers and coating of the reagent composition on the porous layer may be effected by any of the known methods, for example, by dip coating, doctor coating, hopper coating, curtain coating, extrusion coating or multi-layer extrusion coating.

The coated layers may be dried by any known steps, the preferred being the step as disclosed in Unexamined Japanese Patent Publication Nos. 267457/1989 and 267458/1989. The impregnated layers may be dried by similar steps.

The reagent composition may be divided and contained in plural non-porous layer, plural porous layers or in a porous layer and also in a non-porous layer (for example, in the detection layer). For instance, a composition for producing an intermediate product by the reaction with the analyte in the aqueous sample may be contained in a porous layer, and another composition (e.g. an indicator composition) for producing a dye or another optically detectable substance by the reaction with the intermediate product may be contained in a non-porous layer.

The reagent composition may contain an activator, a buffer compostion, a hardener (cross-linking agent) or a surfactant, as desired. Example of the buffer composition which may be contained in the reagent composition used in the analysis element of this invention include carbonates, borates, phosphates or Good buffer composition disclosed in Biochemistry, Vol. 5, No. 2, pages 467 to 477 (1966).

Examples

Some examples of this invention will be described for better understanding of this invention.

EXAMPLE 1

1. Preparation of Dye Solution 63.7 mg of o-cresolphthalein Complexon (OCPC) was dissolved in 30 ml of a 0.02 N NaOH solution, to which added was 0.4 ml of an aqueous solution of $CaCl_2$ containing 10 mg/ml of Ca. The concentration of the used aqueous solution of $CaCl_2$ was inspected using Hitachi #7050 Analyzer (prouced by Hitachi, Ltd.). The thus produced dye, OCPC-Ca chelate compound, was used as a fogging agent.

2. Preparation of Analysis Element

A colorless, transparent and smooth sheet of polyethylene terephthalate having a thickness of 180 μm and coated with an undercoating of gelatine was used as a support on which coated and dried was a solution having the following composition (a) so that a first coating containing respective components in the amounts of distribution parameter (coverage) as set forth below was formed.

| Composition (a) | |
|---|---|
| Deionized Gelatine | 16.8 g/m² |
| Surfactant (Nonylphenoxypolyethoxyethanol; Average Numer of Contained Oxyethylene Unit: 10) | 1.1 g/m² |
| 3-Cyclohexylaminopropane-1-sulfuric Acid | 2.8 g/m² |
| o-Cresolphthalein Complexon | 0.15 g/m² |
| δ-Hydroxyquinoline-5-sulfuric Acid | 0.56 g/m² |
| Dye (OCPC-Ca Chelate Compound Prepared by 1) | 7.1 mg/m² |

(Adjusted to have pH 10.6 with a dilute NaOH solution)

A coating composition having the following compostion (b) was coated on the first coating and then dried to form a second coating (serving as an adhesive layer) containing respective components in the amounts of distribution parameter as set forth below.

| Composition (b) | |
|---|---|
| Deionized Gelatine | 1.46 g/m² |
| Surfactant (Nonylphenoxypolyethoxyethanol; Average Numer of Contained Oxyethylene Unit: 10) | 0.1 g/m² |
| Titanium Dioxide (Fine Particles) | 0.85 g/m² |

(Adjusted to have pH 10.6 with a dilute NaOH solution)

The surface of the adhesive layer was wetted by spraying water (about 30 g/m²) of about 25° C., and then a tricot knitted fabric (36 Gages, Tickness: about 250 microns) made of PET spun threads of 50 deniers was pressed on the wetted adhesive layer, followed by drying, to allow the fabric to adhere onto the adhesive layer.

A solution in ethanol of the separately prepared following composition (c) was coated on the tricot knitted fabric so that the respective components were contained in the amounts of distribution parameter as set forth below.

| Composition (c) | |
|---|---|
| Polyvinyl Pyrrolidone (Average Molecular Weight: 360,000) | 4.1 g/m² |
| Nonylphenoxypolyethoxyethanol (Average Number of Contained Oxyethylene Unit: 40) | 8.6 g/m² |
| Citric Acid | 0.6 g/m² |
| Solvent: Ethanol | |

The content of calcium in the deionized gelatine used in Example 1 was 7 ppm.

The quantity of the dye (OCPC-Ca chelate compound) added to the composition (a) which formed an indicator layer, i.e. 7.1 mg/m², was calculated by subtracting the blank value obtained by a preliminary test of an analysis element, which was prepared similarly as in Example 1 except that the dye solution was not added, from the blank value of the internal calibration curve memorized in the analyzer which will be described hereinafter.

COMPARATIVE EXAMPLE 1

An analysis element was prepared similar to Example 1 except that the dye, OCPC-Ca chelate compound, was not added.

EXAMPLE 2

Generally following the procedure as described in Example 1, except that a deionized gelatine containing 22 ppm of calcium was used and that the amount of the added dye (OCPC-Ca chelate compound) was controlled to have a distribution parameter (coverage) of 2.4 mg/m² so that the blank value of the analysis element was agreed with the blank value of the internal calibration curve.

COMPARATIVE EXAMPLE 2

An analysis element was prepared similar to Example 2 except that the dye solution was not added.

MEASUREMENT EXAMPLE 1

Using the analysis elements prepared by Examples 1 and 2 and Comparative Examples 1 and 2, the concentration of calcium in a Monitorol Ix (Content of Ca: 9.5 mg/dl) was measured. The results are shown in Table 1. Fuji Drychem 5000 Analyzer produced by Fuji Photo Film Co., Ltd. was used for spotting of the control sample, incubating and optical density measurement.

TABLE 1

| Ca content in Gelatine | Used Analysis Element | Ca content Measured |
| --- | --- | --- |
| 7 ppm | Example 1 | 9.3 mg/dl |
| 22 ppm | Example 2 | 9.7 mg/dl |
| 7 ppm | Comparative Example 1 | 7.5 mg/dl |
| 22 ppm | Comparative Example 2 | 9.1 mg/dl |

As will be seen from the results set forth in Table 1, the results of measurement (the Ca contents in the samples) were varied only slightly when the analysis elements of the present invention were used irrespective of change in calcium content in the used gelatine. On the contrary, when the analysis elements of Comparative Examples were used, the results of measurements were varied significantly as the calcium contents in the used gelatine were changed.

EXAMPLE 3

A colorless, transparent and smooth sheet of polyethylene terephthalate having a thickness of 180 microns and coated with an undercoating of gelatine was used as a support on which coated and dried was a solution having the following composition (a) so that a first coating (serving as a water-absorbing layer) containing respective components in the amounts of distribution parameter as set forth below was formed.

| Composition (a) | |
| --- | --- |
| Polyvinyl Alcohol (Average Molecular Weight: 360,000) | 22.0 g/m² |
| Nonylphenoxypolyethoxyethanol (Average Number of Contained Oxyethylene Unit: 40) | 0.28 g/m² |
| Zinc sulfate | 1.8 g/m² |
| Sodium Naphthalenedisulfonate | 1.8 g/m² |
| Surfactant (Aerosol OT; Di(2-ethylhexyl)-sulfosuccinate Na Salt) | 0.23 g/m² |
| Sulfosalicylic Acid | 0.64 g/m² |
| Hardener (Tetramethylene-1,4-diol bis(glycidyl ether)) | 0.74 g/m² |

The lot number of the used polyvinyl alcohol was Lot No. 1.

After wetting the surface of the thus formed adhesive layer with water of about 25° C. substantially uniformly, a tricot knitted fabric composed of PET spun threads of 100 S and having a thickness of about 250 microns was pressed onto the adhesive layer, followed by drying, to allow the fabric to adhere to the adhesive layer.

The following composition (b) was coated to be impregnated into the knitted fabric and dried.

| Composition (b) | |
| --- | --- |
| Diphyline [CA Registry No. 479-18-5] | 19.0 g/m² |
| Poly(2-acrylamide-2-methylpropane Sulfonic Acid) | 3.1 g/m² |
| Sodium Naphthalenedisulfonate | 0.74 g/m² |
| Sodium Di-2-ethylhexylsulfosuccinate | 0.4 g/m² |
| Sulfosalicylic Acid Dihydrate | 7.42 g/m² |
| 2,4-Dichlorobenzenediazonium Sulfosalycylate | 0.86 g/m² |
| 1,8-Dihdroxy-2-(2,4-dichlorophenylazo)-naphthalene-3,6-disulfonic Acid | 12.3 mg/m² |
| Solvent: Water | |

EXAMPLE 4

Generally following the procedure as described in Example 3, except that a Lot No. 2 polyvinyl alcohol was used in place of the Lot No. 1 polyvinyl alcohol and that the amount of the added dye in the coating composition (b), i.e. 1,8-Dihydroxy-2-(2,4-dichlorophenylazo)naphthalene-3,6-disulfonic acid, was decreased so that the distribution parameter thereof became 5.3 mg/m².

COMPARATIVE EXAMPLE 3

An analysis element was prepared similar to Example 3 except that the dye solution was not added.

COMPARATIVE EXAMPLE 4

An analysis element was prepared similar to Example 4 except that the dye solution was not added.

MEASUREMENT EXAMPLE 2

Using the analysis elements prepared by Examples 3 and 4 and Comparative Examples 3 and 4, the concentration of bilirubin in a Monitorol Ix (Content of bilirubin: 0.83 mg/dl) was measured. Fuji Drychem 5000 Analyzer (produced by Fuji Photo Film Co., Ltd.) was used for spotting of the control sample, incubating and optical density measurement. The results are shown in Table 2.

TABLE 2

| Lot No. of Used Polyvinyl Alcohol | Used Analysis Element | Concentration of Bilirubin Measured |
| --- | --- | --- |
| Lot No. 1 | Example 3 | 0.72 mg/dl |
| Lot No. 2 | Example 4 | 0.85 mg/dl |
| Lot No. 1 | Comparative Example 3 | 0.22 mg/dl |
| Lot No. 2 | Comparative Example 4 | 0.79 mg/dl |

As will be seen from the results set forth in Table 2, the results of measurement (measured concentrations of bilirubin) were varied only slightly when the analysis elements of the present invention were used notwithstanding that different lots of polyvinyl alcohol were used. On the contrary, when the analysis elements of Comparative Examples were used, the results of measurements were varied significantly as different polyvinyl alcohol lots were used.

What is claimed is:

1. An analysis element comprising a water-permeable layer which contains:
   a reagent composition capable of producing an optically detectable substance in the presence of a predetermined analyte in an aqueous sample; and
   a fogging agent which is detectable by the same method and at the same wavelength as that for detecting said optically detectable substance, said fogging agent being capable of raising the blank level at said wavelength of the element to a predetermined constant level,
   wherein said fogging agent and said optically detectable substance are identical.

2. The analysis element of claim 1, wherein said water-permeable layer is comprised of a porous medium.

3. The analysis element of claim 1, wherein said water-permeable layer is comprised of a non-porous medium.

4. The analysis element of claim 3, wherein said water-permeable layer is laminated on a support.

5. The analysis element of claim 3, wherein said non-porous medium is a hydrophilic polymer binder.

6. An analysis element comprising:
   a first water-permeable layer containing a reagent composition capable of producing an optically detectable substance in the presence of a predetermined analyte in an aqueous sample, and
   a second water-permeable layer containing a fogging agent which is detectable by the same method and at the same wavelength as that for detecting said optically detectable substance, said fogging agent being capable of raising the blank level at said wavelength of the element to a predetermined constant level,
   wherein said fogging agent and said optically detectable substance are identical.

7. The analysis element of claim 6, wherein said second water-permeable layer is comprised of a porous medium.

8. The analysis element of claim 6, wherein said second water-permeable layer is comprised of a non-porous medium.

9. The analysis element of claim 8, wherein said second water-permeable layer is laminated on a support.

10. The analysis element of claim 8, wherein said non-porous medium is a hydrophilic polymer binder.

11. In a process for preparing an analysis element comprising a water-permeable layer containing a reagent composition capable of producing an optically detectable substance in the presence of a predetermined analyte in an aqueous sample,
    an improved process which comprises the step of adding a fogging agent which is detectable by the same method and at the same wavelength as that for detecting said optically detectable substance to said water-permeable layer, said fogging agent being capable of raising the blank level at said wavelength of the element to a predetermined constant level,
    wherein said fogging agent and said optically detectable substance are identical.

12. The process of claim 11, wherein said water-permeable layer is comprised of a porous layer and said fogging agent is impregnated into said porous layer.

13. The process of claim 12, wherein said fogging agent is impregnated into said porous layer together with said reagent composition.

14. The process of claim 12, wherein said fogging agent is impregnated into said porous layer by a step which is independent from the step of impregnating said reagent composition.

15. The process of claim 11, wherein said water-permeable layer is comprised of a non-porous medium laminated on a support, and said fogging agent is added to said non-porous medium and applied on said support together with said non-porous medium.

16. The process of claim 15, wherein said fogging agent is added to said non-porous medium together with said reagent composition and applied on said support together with said non-porous medium.

17. The process of claim 11, wherein said water-permeable layer is comprised of a non-porous medium which is laid on another water-permeable layer, and said fogging agent is added to said non-porous medium and applied on said support together with said non-porous medium.

18. The process of claim 17, wherein said fogging agent is added to said non-porous medium together with said reagent composition and applied on said support together with said non-porous medium.

19. In a process for preparing an analysis element comprising at least two water-permeable layers, the first water-permeable layer containing a reagent composition capable of producing an optically detectable substance in the presence of a predetermined analyte in an aqueous sample,
    an improved process which comprises the step of preparing a second water permeable layer by adding a fogging agent which is detectable by the same method and at the same wavelength as that for detecting said optically detectable substance, said fogging agent being capable of raising the blank level at said wavelength of the element to a predetermined constant level,
    wherein said fogging agent and said optically detectable substance are identical.

20. The process of claim 19, wherein said second water permeable layer is comprised of a porous layer and said fogging agent is impregnated into said porous layer.

21. The process of claim 19, wherein said second water-permeable layer is comprised of a non-porous medium laminated on a support, and said fogging agent is added to said non-porous medium and applied on said support together with said non-porous medium.

22. The process of claim 19, wherein said second water-permeable layer is comprised of a non-porous medium which is laminated on another water-permeable layer, and said fogging agent is added to said non-porous medium and applied on said another water-permeable layer together with said non-porous medium.

* * * * *